US009216242B2

(12) United States Patent
Nishtala et al.

(10) Patent No.: US 9,216,242 B2
(45) Date of Patent: *Dec. 22, 2015

(54) MULTI-FUNCTIONAL AND MODULAR URINE COLLECTION SYSTEM

(75) Inventors: Vasu Nishtala, Snellville, GA (US); Warren F. Taylor, Conyers, GA (US); Robert M. Hine, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1284 days.

This patent is subject to a terminal disclaimer.

(21) Appl. No.: 13/076,329

(22) Filed: Mar. 30, 2011

(65) Prior Publication Data

US 2011/0178425 A1    Jul. 21, 2011

Related U.S. Application Data

(63) Continuation of application No. 11/175,578, filed on Jul. 5, 2005, now Pat. No. 7,931,630.

(51) Int. Cl.
| | | |
|---|---|---|
| *A61M 1/00* | (2006.01) | |
| *A61B 5/145* | (2006.01) | |
| *A61B 5/20* | (2006.01) | |
| *A61B 5/15* | (2006.01) | |
| *G05D 13/00* | (2006.01) | |
| *B60K 15/06* | (2006.01) | |
| *G05D 16/10* | (2006.01) | |
| *A61F 5/44* | (2006.01) | |

(52) U.S. Cl.
CPC .......... *A61M 1/0031* (2013.01); *A61B 5/14507* (2013.01); *A61B 5/20* (2013.01); *A61B 5/208* (2013.01); *A61M 1/0001* (2013.01); *A61M 1/0015* (2014.02); *A61F 5/44* (2013.01)

(58) Field of Classification Search
CPC ........... A61M 1/0013; A61M 5/15003; G05D 13/00; G05D 16/10; B60K 15/06; F04B 39/1033; F16L 15/038; F16K 15/16; B67D 7/163; B67D 7/763; A01K 5/0291; A47G 19/24

See application file for complete search history.

(56) References Cited

U.S. PATENT DOCUMENTS

| | | | | |
|---|---|---|---|---|
| 2,702,034 | A | * | 2/1955 | Walter .......................... 604/262 |
| 3,187,750 | A | * | 6/1965 | Tenczar, Jr. ................... 604/410 |
| 3,194,069 | A | | 7/1965 | Scott |
| 3,345,980 | A | | 10/1967 | Meisch |

(Continued)

FOREIGN PATENT DOCUMENTS

| | | |
|---|---|---|
| CN | 102112071 A | 6/2011 |
| GB | 2134789 A | 8/1984 |

(Continued)

OTHER PUBLICATIONS

CN 200980130883.5 First Office Action dated Sep. 13, 2012.

(Continued)

*Primary Examiner* — Tatyana Zalukaeva
*Assistant Examiner* — Ilya Treyger
(74) *Attorney, Agent, or Firm* — Rutan & Tucker, LLP

(57) ABSTRACT

Multi-functional urine collection devices, embodiments of which can include a self-expanding container having a receptacle for receiving urine from the tubing, a pump for moving urine through the tubing and into a receptacle, extendable tubing that may be shortened and/or lengthened, and/or one or more meters for monitoring, measuring, transmitting or storing a characteristic from the urine.

20 Claims, 6 Drawing Sheets

(56) References Cited

U.S. PATENT DOCUMENTS

| | | | |
|---|---|---|---|
| 3,362,400 A * | 1/1968 | De Bella | 600/575 |
| 3,561,427 A | 2/1971 | Profy | |
| 3,566,930 A * | 3/1971 | Kirschner | 141/244 |
| 3,650,272 A | 3/1972 | Ericson | |
| 3,661,143 A | 5/1972 | Henkin | |
| 3,699,964 A | 10/1972 | Ericson | |
| 3,703,731 A * | 11/1972 | Leiser | 4/144.3 |
| 3,721,243 A | 3/1973 | Henkin | |
| 3,722,502 A | 3/1973 | Besuner et al. | |
| 3,752,393 A * | 8/1973 | Moseley | 702/45 |
| 3,831,453 A | 8/1974 | McWhorter | |
| 3,848,581 A * | 11/1974 | Cinqualbre et al. | 600/575 |
| 3,943,929 A | 3/1976 | Patel | |
| 3,961,529 A | 6/1976 | Hanifl | |
| 3,974,533 A * | 8/1976 | Klecker | 4/455 |
| 3,982,898 A | 9/1976 | McDonald | |
| 4,000,649 A * | 1/1977 | Hanifl | 600/575 |
| 4,015,605 A | 4/1977 | McWhorter | |
| 4,042,337 A | 8/1977 | Griffith | |
| 4,057,062 A | 11/1977 | Lavigne | |
| 4,126,135 A * | 11/1978 | Hinman, Jr. | 604/326 |
| 4,178,934 A | 12/1979 | Forman | |
| 4,194,509 A | 3/1980 | Pickering et al. | |
| 4,202,058 A * | 5/1980 | Anderson | 4/144.3 |
| 4,206,767 A | 6/1980 | Wingrove | |
| 4,227,533 A | 10/1980 | Godfrey | |
| 4,265,118 A * | 5/1981 | Griesel | 73/427 |
| 4,291,706 A | 9/1981 | Voges et al. | |
| 4,305,290 A | 12/1981 | Taylor | |
| 4,305,405 A | 12/1981 | Meisch | |
| 4,312,352 A | 1/1982 | Meisch et al. | |
| 4,313,447 A | 2/1982 | Peterson et al. | |
| 4,334,537 A | 6/1982 | Peterson | |
| 4,343,316 A | 8/1982 | Jespersen | |
| 4,386,930 A | 6/1983 | Cianci | |
| 4,388,922 A | 6/1983 | Telang | |
| 4,391,780 A * | 7/1983 | Boris | 422/550 |
| 4,423,741 A | 1/1984 | Levy | |
| 4,435,171 A | 3/1984 | Goldberg et al. | |
| 4,443,219 A | 4/1984 | Meisch et al. | |
| 4,447,939 A | 5/1984 | Taylor | |
| 4,452,253 A | 6/1984 | Peterson et al. | |
| 4,460,362 A | 7/1984 | Bates | |
| 4,473,530 A | 9/1984 | Villa-Real | |
| 4,490,863 A * | 1/1985 | Pate | 4/301 |
| 4,534,341 A | 8/1985 | Bart et al. | |
| 4,583,972 A * | 4/1986 | Hunter et al. | 604/133 |
| 4,590,800 A | 5/1986 | Shimoda | |
| 4,610,781 A * | 9/1986 | Bilstad et al. | 210/85 |
| 4,654,029 A | 3/1987 | D'Antonio | |
| 4,659,329 A | 4/1987 | Annis | |
| 4,661,100 A | 4/1987 | Rechsteiner | |
| 4,683,598 A * | 8/1987 | Jones | 4/301 |
| 4,685,480 A | 8/1987 | Eck | |
| 4,699,155 A * | 10/1987 | Villari et al. | 600/575 |
| 4,723,950 A | 2/1988 | Lee | |
| 4,728,324 A | 3/1988 | Steigerwald et al. | |
| 4,753,249 A | 6/1988 | Muller | |
| 4,770,445 A | 9/1988 | Steer et al. | |
| 4,815,477 A | 3/1989 | McWhorter et al. | |
| 4,819,653 A | 4/1989 | Marks | |
| 4,850,560 A | 7/1989 | Ross | |
| 4,865,046 A * | 9/1989 | Duran | 600/575 |
| 4,889,533 A | 12/1989 | Beecher | |
| 4,913,161 A | 4/1990 | Villari et al. | |
| 4,981,474 A | 1/1991 | Bopp et al. | |
| 5,165,647 A | 11/1992 | Ribeiro | |
| 5,265,118 A | 11/1993 | Takenaka et al. | |
| 5,331,689 A | 7/1994 | Haq | |
| 5,375,799 A | 12/1994 | Rhodes | |
| 5,397,299 A | 3/1995 | Karwoski et al. | |
| 5,451,218 A * | 9/1995 | Moore | 604/317 |
| 5,454,798 A | 10/1995 | Kubalak et al. | |
| 5,549,707 A | 8/1996 | Weaver | |
| 5,616,138 A | 4/1997 | Propp | |
| 5,891,051 A | 4/1999 | Han et al. | |
| 6,129,714 A | 10/2000 | Kocsi | |
| 6,132,407 A | 10/2000 | Genese et al. | |
| 6,240,960 B1 | 6/2001 | Fillmore | |
| 6,261,254 B1 * | 7/2001 | Baron et al. | 604/323 |
| 6,481,462 B2 | 11/2002 | Fillmore et al. | |
| 6,582,379 B1 | 6/2003 | Stisen | |
| 6,641,562 B1 | 11/2003 | Peterson | |
| 6,652,495 B1 | 11/2003 | Walker | |
| 6,800,074 B2 | 10/2004 | Henley et al. | |
| 6,849,070 B1 | 2/2005 | Hansen et al. | |
| 6,887,223 B2 | 5/2005 | Bisbee | |
| 7,585,293 B2 | 9/2009 | Vermaak | |
| 7,931,630 B2 * | 4/2011 | Nishtala et al. | 604/318 |
| 8,650,669 B1 * | 2/2014 | Kolter | 4/144.1 |
| 2001/0037097 A1 | 11/2001 | Cheng et al. | |
| 2002/0087131 A1 | 7/2002 | Wolff et al. | |
| 2004/0132091 A1 | 7/2004 | Ramsey et al. | |
| 2004/0176703 A1 | 9/2004 | Christensen et al. | |
| 2005/0119630 A1 | 6/2005 | Harvie | |
| 2006/0189926 A1 * | 8/2006 | Hall et al. | 604/66 |
| 2007/0010797 A1 | 1/2007 | Nishtala et al. | |
| 2008/0271796 A1 * | 11/2008 | Neumann et al. | 137/606 |
| 2008/0312550 A1 | 12/2008 | Nishtala et al. | |
| 2009/0157016 A1 | 6/2009 | Adahan | |
| 2010/0137743 A1 | 6/2010 | Nishtala et al. | |
| 2011/0251572 A1 | 10/2011 | Nishtala et al. | |
| 2013/0218106 A1 | 8/2013 | Coston et al. | |

FOREIGN PATENT DOCUMENTS

| | | |
|---|---|---|
| JP | 09-024105 | 1/1997 |
| JP | 3053305 U | 10/1998 |
| JP | 2002-156376 A | 5/2002 |
| JP | 2011-522624 A | 8/2011 |
| JP | 2012254306 A | 12/2012 |
| JP | 5192375 | 2/2013 |
| WO | 03105942 A1 | 12/2003 |
| WO | 2007005851 A2 | 1/2007 |
| WO | 2009149387 A1 | 12/2009 |
| WO | 2012016179 A1 | 2/2012 |

OTHER PUBLICATIONS

JP 2008-520338 filed Jan. 4, 2008 Office Action dated Jan. 26, 2012.
JP 2008-520338 filed Jan. 4, 2008 Office Action dated May 26, 2011.
PCT/US11/45956 filed Jul. 29, 2011 International Search Report dated Dec. 16, 2011.
PCT/US11/45956 filed Jul. 29, 2011 Written Opinion dated Dec. 16, 2011.
PCT/US2009/046472 filed Jun. 5, 2009, Search Report dated Jul. 21, 2009.
PCT/US2009/046472 filed Jun. 5, 2009, Written Opinion dated Jul. 21, 2009.
U.S. Appl. No. 12/689,870, filed Jan. 19, 2010 Non-Final Office Action dated Jan. 16, 2013.
U.S. Appl. No. 12/689,870, filed Jan. 19, 2010 Non-Final Office Action dated Oct. 11, 2012.
U.S. Appl. No. 12/996,595, filed Jun. 29, 2011 Final Office Action dated Feb. 15, 2013.
U.S. Appl. No. 12/996,595, filed Jun. 29, 2011 Non-Final Office Action dated Aug. 28, 2012.
AU 2006265085 filed Jan. 4, 2008 Examiner's First Report dated Mar. 8, 2012.
AU 2006265085 filed Jan. 4, 2008 Notice of Acceptance dated Jul. 20, 2012.
CA 2,614,366 filed Jan. 4, 2008 Office Action dated Jul. 30, 2012.
EP 06774478.9 filed Jan. 16, 2008 European Examination Report dated Oct. 16, 2009.
PCT/US2006/026011 filed Jun. 29, 2006 International Preliminary Report on Patentability dated Jan. 9, 2008.
PCT/US2006/026011 filed Jun. 29, 2006 International Search Report dated Mar. 8, 2007.
PCT/US2006/026011 filed Jun. 29, 2008 Written Opinion dated Mar. 8, 2007.

(56) References Cited

OTHER PUBLICATIONS

U.S. Appl. No. 11/175,578, filed Jul. 5, 2005 Final Office Action dated Mar. 26, 2008.
U.S. Appl. No. 11/175,578, filed Jul. 5, 2005 Final Office Action dated Nov. 3, 2006.
U.S. Appl. No. 11/175,578, filed Jul. 5, 2005 Non-Final Office Action dated Jan. 8, 2009.
U.S. Appl. No. 11/175,578, filed Jul. 5, 2005 Non-Final Office Action dated Jun. 16, 2010.
U.S. Appl. No. 11/175,578, filed Jul. 5, 2005 Non-Final Office Action dated May 11, 2007.
U.S. Appl. No. 11/175,578, filed Jul. 5, 2005 Non-Final Office Action dated May 4, 2006.
U.S. Appl. No. 11/994,575, filed Jul. 21, 2008 Advisory Action dated Aug. 31, 2012.
U.S. Appl. No. 11/994,575, filed Jul. 21, 2008 Advisory Action dated Aug. 4, 2010.
U.S. Appl. No. 11/994,575, filed Jul. 21, 2008 Final Office Action dated Jun. 14, 2012.
U.S. Appl. No. 11/994,575, filed Jul. 21, 2008 Final Office Action dated May 25, 2010.
U.S. Appl. No. 11/994,575, filed Jul. 21, 2008 Non-Final Office Action dated Jun. 17, 2009.
U.S. Appl. No. 11/994,575, filed Jul. 21, 2008 Non-Final Office Action dated May 9, 2011.
U.S. Appl. No. 12/689,870, filed Jan. 19, 2010 Final Office Action dated Dec. 12, 2011.
U.S. Appl. No. 12/689,870, filed Jan. 19, 2010 Non-Final Office Action dated Jun. 24, 2011.
U.S. Appl. No. 12/689,870, filed Jan. 19, 2010 Notice of Panel Decision dated Jun. 29, 2012.
CN 200980130883.5 Second Office Action dated Jul. 29, 2013.
JP 2011-512709 Office Action dated May 27, 2013.
JP 2012-163542 filed Jul. 24, 2012 Office Action dated Aug. 27, 2013.
JP 2012-163542 filed Jul. 24, 2012 Office Action dated Mar. 13, 2014.

* cited by examiner

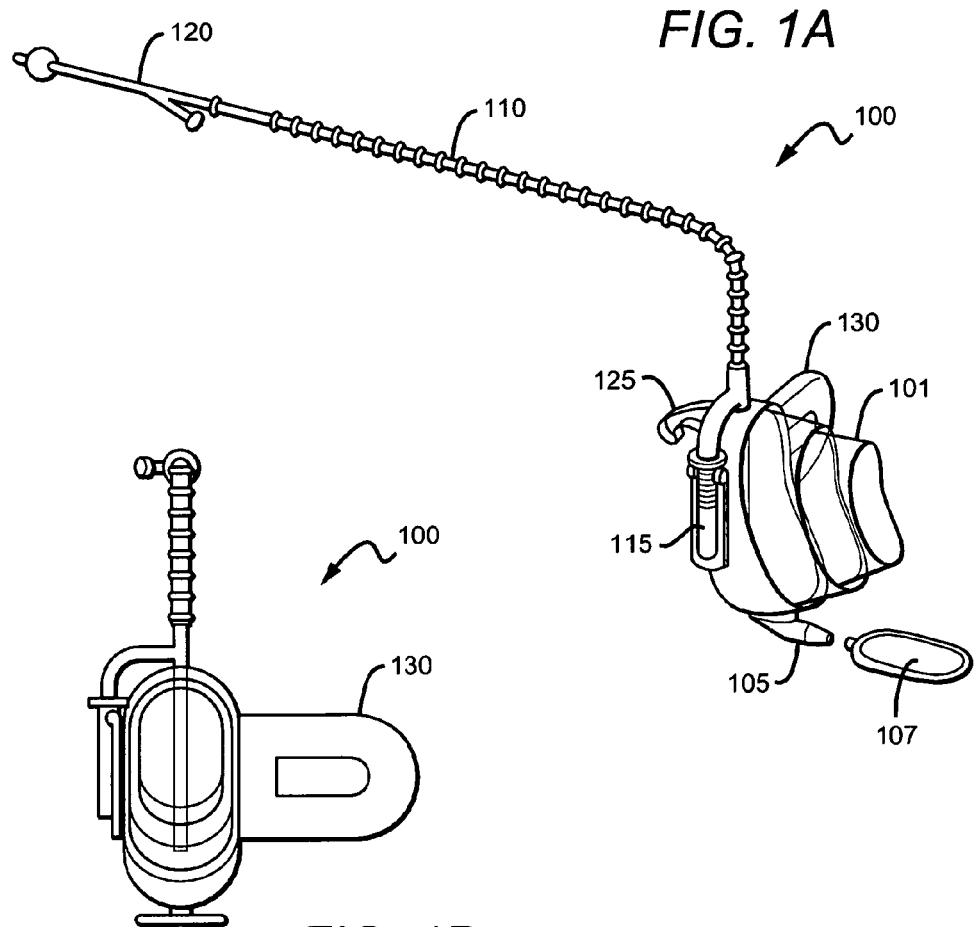
FIG. 1A
FIG. 1B
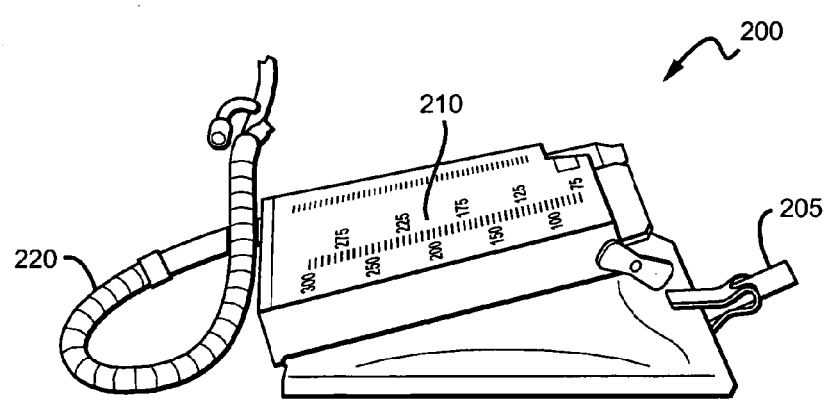
FIG. 2A

FIG. 2B
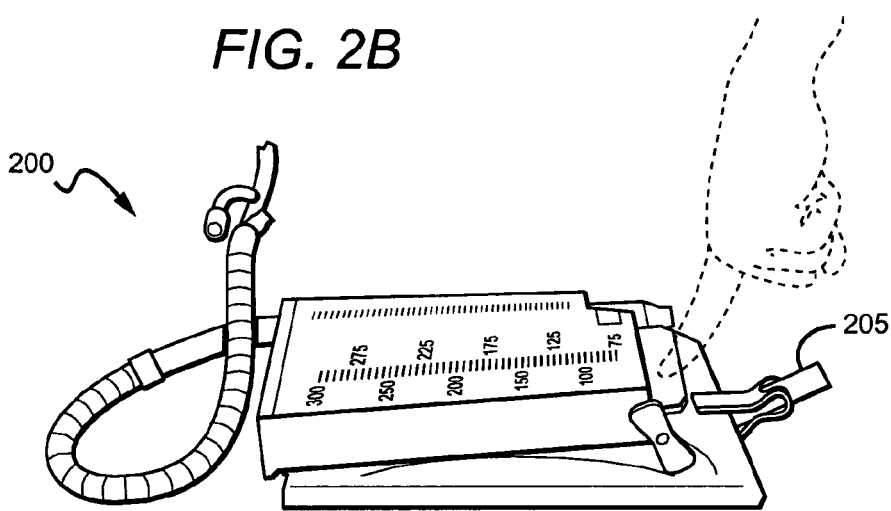
FIG. 3A
FIG. 3B
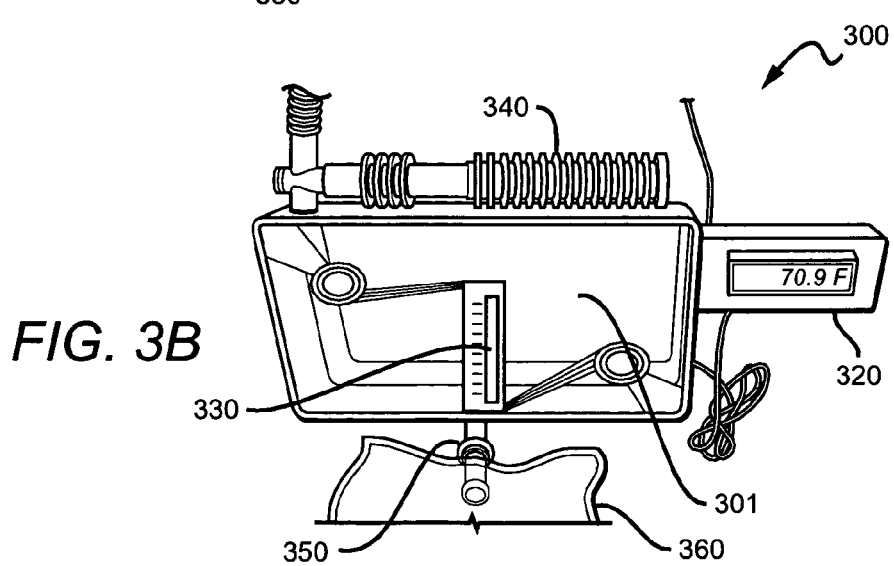

MULTI-FUNCTIONAL AND MODULAR URINE COLLECTION SYSTEM

PRIORITY

This application is a continuation of U.S. application Ser. No. 11/175,578, now U.S. Pat. No. 7,931,630, filed Jul. 5, 2005, which is incorporated by reference into this application as if fully set forth herein.

BACKGROUND

Urinary drainage bags are conventionally used in hospitals and health care facilities when it is necessary to collect urine from a catheterized patient over an extended period of time. Such bags are routinely used by post-operative patients as well as those with urological disorders for collection, measuring, and testing the frequency of urinary output. Urinary drainage systems typically include a catheter with tubing attached thereto, connected to a collection bag made of a polymeric material such as a PVC film. The collection bag generally includes a component for emptying the bag, such as a drainage tube. In operation, the patient is first catheterized, and the catheter is then connected to the drainage bag through a length of tubing. The bag is normally supported either from the bed rail or other support structure (usually below the level of the patient), the urine draining through the catheter, the tubing, and then finally into the bag due to gravitational forces. Most bags are provided with drain ports through which measured quantities of urine can be removed for various testing procedures.

Typical urine drainage bags are described in U.S. Pat. No. 3,650,272 (titled "Drainage Bag," issued Mar. 21, 1972), U.S. Pat. No. 4,312,352 (titled "Hanger, hook and handle assembly for urinary drainage bag," issued Jan. 26, 1982), U.S. Pat. No. 4,313,447 (titled "Collection bag," issued Feb. 2, 1982), U.S. Pat. No. 4,386,930 (titled, "Collection device for body fluids with antiseptic pump," issued Jun. 7, 1983), U.S. Pat. No. 4,443,219 (titled "System for aseptically draining a urine bag," issued Apr. 17, 1984), U.S. Pat. No. 4,452,253 (titled, "Collection bag," issued Jun. 5, 1984), U.S. Pat. No. 4,659,329 (titled, "Liquid drainage system," issued Apr. 21, 1987), U.S. Pat. No. 4,723,950 (titled, "Urine drainage bag outlet with barrier against microbial infection," issued Feb. 9, 1988), U.S. Pat. No. 5,375,799 (titled, "Collection bag hanger with rail width-adjustable hook arms," issued Dec. 27, 1994), and U.S. Pat. No. 5,454,798 (titled, "Disposable urine bag," issued Oct. 3, 1995), each of which is herein incorporated by reference in its entirety.

One of the potential drawbacks with typical urine collection bags is the possibility of contamination and infection to the patient. In particular, when the bags are opened to remove some or all of the urine, air may be permitted to enter into the outlet spout, allowing bacteria to migrate up the spout into the bag, and finally into the bladder, causing infection. Additionally, there may be the problem of contamination of hospital personnel due to leakage or splattering of urine during the collection process. Urine may also collect in the tubing connecting the catheter to the urine collection bag, referred to as urine stasis or hold up within the tubing. For example, urine may stand in the tubing because the pressure expelling the urine down the tube into the collection bag is less than the pressure required to empty the tubing into the collection bag.

In traditional urine collection systems, urine is moved from the catheter into the collection bag solely due to gravitational forces. Thus, evacuation of urine from the catheter and/or tubing may be prevented when the tubing pathway is not directed downward (e.g., if the tubing is lying flat, or if a portion of the tubing is not above the collection bag). Urine collection within the tubing is undesirable and may contribute to infection, spilling and/or urine reflux. Furthermore, some urine collection systems analyze urine from urine collected in the collection bag, meaning that urine collected within the catheter and/or tubing may prevent accurate measurement/analysis. On average, about 80-90 mL of urine are produced in 1 hour. This is approximately the same volume required to fill the current commercially available drainage tubing. Standing urine in the tubing is undesirable both from a possible retrograde infection standpoint and because it necessitates spending time and resources to clear the tubing. It is hypothesized that not having collected urine in the tubing will aid in infection control and reduce patient exposure and hospital costs.

BRIEF SUMMARY OF THE INVENTION

Accordingly, described herein are urine collection devices (including bags), systems of collecting urine, methods of making and using urine collection bags, and kits comprising urine collection bags. The urine collection devices and systems described herein allow unattended drainage, and may prevent urine stasis and reflux. Further, these urine collection devices and systems may allow collection of urine even against gravity, and may provide a closed, non-contact system for collecting and disposing of waste urine. Although the discussions, systems and methods of use described herein are all described for urine and urine collection, the same concepts and ideas may be applied to draining other bodily fluid applications, including wound drains, etc.

In general, urine collection devices may include a receptacle to collect urine (e.g., a bag, a box, a pouch, or any appropriate container) having an inlet through with urine enters the receptacle, and tubing connected to the inlet for transporting urine from a subject into the receptacle. The urine collection devices described herein are adapted to prevent retention of urine within the tubing. For example, urine collection devices and systems described herein may include a self-expanding container having a receptacle for receiving urine from the tubing, a pump for moving urine through the tubing and into a receptacle, extendable tubing that may be shortened and/or lengthened, and one or more meters for monitoring, measuring, transmitting or storing a characteristic from the urine. In one variation, the urine collection device includes an expandable container forming a receptacle, the container having a contracted position and an expanded position, and a bias for converting the container from the contracted position to the expanded position. The urine collection device also may include an inlet into the receptacle formed by the container through which urine can enter. The expandable container may be self-expanding.

The bias may be part of the container or it may be a separate biasing element. For example, the walls of the container may be made of a material having a shape memory so that the container will self-expand from a contracted position (e.g., at least partially closed), into an expanded position (e.g., mostly open). A separate biasing element such as a spring (e.g., a leaf spring) may be included as part of the expandable container to expand the container from the collapsed to expanded configuration. A holdfast (e.g., a latch, hook, fastener, strap, etc.) may be used to secure the expandable container in either the expanded or collapsed configuration (or both). For example, the expandable container may be secured in the collapsed configuration; releasing the expandable container from the collapsed configuration allows the container to automatically expand into the expanded configuration.

In some variations, the urine collection device may include an outlet port through which urine may be removed from the receptacle. The outlet port may include tubing. The outlet port may also have an outlet valve. In some variations, the outlet valve mates with a specific receiving device (e.g., a disposable bag, or a transport container) so that urine can only empty through the outlet valve when it is properly mated, preventing accidental spilling of urine. In some variations, the urine collection device is disposable, or configured for a single use. The urine collection device having an expandable container may be part of a system including: a meter, a pump, outlet valves, air inlets/outlets, extendable tubing, etc. Any combination of these components may be included with the expandable container.

Also described herein are methods of collecting urine from a subject having a urinary catheter (e.g., a Foley catheter). The methods include releasing a urine collection device from a contracted position into an expanded position, in which the urine collection device includes a self-expanding (e.g., expandable) container forming a receptacle. The container has a contracted position, an expanded position, and a bias to convert the container from the contracted position to the expanded position. The method may also include connecting the urine collection device to a urinary catheter.

Also described herein are meters for measuring at least one characteristic from urine, the meter including a measurement region for holding urine and a meter release to control the emptying of urine from the measurement region into the receptacle. The measurement region may be calibrated, for example, by including calibration markings that can be read by an observer or recording device. Thus, the measurement region may include a series of graduated regions that show the volume of urine. In some variations, the measurement region includes a sensor or sensors, for detecting some characteristic of the urine. Any appropriate sensor may be used, including optical, electrical, sonic, temperature, etc.

The meter (e.g., the measurement region) may include a plurality of ports that connect the meter to the receptacle region of the urine collection device through which the urine may be emptied from the meter. A manual or automatic meter release (e.g., a switch, lever, button, etc.) triggers the emptying of the meter region into the receptacle. In some variations, the meter is connected to the receptacle and the inlet that can connect to tubing (and ultimately to a subject from whom urine is being collected). Urine may empty though the inlet and into the meter, where some characteristic of the urine is measured. For example, the meter may measure the volume of urine released (e.g., over a period of time), the flow rate of urine released, the pH of the urine, the temperature, and/or the presence or concentration of a compound in the urine (e.g., urea, salts, toxins, etc.). Any appropriate measurement may be made. After completing a measurement, the urine can be emptied from the meter (e.g., the measurement region of the meter) into the receptacle, where the urine may be stored until it is emptied from the receptacle, or until the urine collection device is removed.

Also described herein are urine collection devices and systems including a pump configured to move urine through the tubing of urine collection device. Any appropriate pump may be used, including an impeller pump. The pump may be controlled either automatically, manually or both. In some variations, the pump may be controlled by a sensor that detects urine within the tubing. In some variations, the pump is controlled by a timer, so that it turns on/off at settable intervals. The pump may apply positive (blowing) or negative (vacuum) force to move urine down the tubing. In some variations, the pump is connected to the tubing portion of the urine collection device (e.g., near the catheter attachment region, near the inlet of the receptacle/meter, or between these positions). However, the pump may also be connected to a meter region, or to the receptacle, so that it can draw (e.g., by negative pressure) urine from the tubing.

Urine collection devices and systems including a pump may also include one or more air inlets or outlets for regulating the pressure (e.g., air pressure) within the urine collection device. An air inlet or outlet may be an air inlet/outlet valve, such as a one-way valve. Air inlet and/or outlet ports may be positioned so that the pump moves urine down the tubing and ultimately into the receptacle for holding the urine without allowing leakage of urine from the urine collection device and without applying positive or negative pressure to the catheter or a subject wearing a catheter. The pump may be battery powered, and may be disposable, or configured for a single use.

Also described herein are urine collection devices and system including extendable tubing. Extendable tubing may provide a fluid pathway for urine, allowing urine to drain from a catheter and into the receptacle of a urine collection device (including through an inlet and/or a meter). Extendable tubing is typically flexible. In general, extendable tubing (or adjustable tubing) includes a compressed length and an extended length that is longer than the compressed length, and may be adjusted to be any appropriate length between the extended and compressed lengths. The extendable tubing may have an outer surface and an inner surface. The inner surface may be substantially free of wall irregularities where urine may be retained. For example, the inner wall may be smooth, and may include an elastomeric material, so that it can extend between the compressed and the extended lengths. In some variations, the inner wall includes the inner lumen of an elastomeric tube that is surrounded by an adjustable outer wall. The outer wall is adjustable to vary the length of the tubing. For example, the outer wall may be made from regions that change their position or conformation relative to each other to lengthen or shorten the tubing. The outer wall may include segments that telescope to shorten or lengthen, by sliding inward or outward in overlapping sections. In some variations, the outer wall includes regions that are hinged so that they move, accordion-like, to shorten or lengthen the tubing. In some variations, the outer wall and the inner wall are integral regions of the same tubing.

As described herein, extendable tubing can hold or maintain whatever length it is adjusted to over time without contracting or expanding back to a resting state (unlike simple elastomeric tubing). Expandable tubing may be configured to expand more than 1.5 times the compressed length of the tubing. For example, expandable tubing may be able to expand more than 2 times, 2.5 times, 3 times, 5 times, or 10 times the length of the collapsed length. In some variations, the tubing (e.g., the inner wall of the tubing that contacts urine) may include a material that decreases any retention of urine by the walls of the tubing. For example, the inner surface of the tubing may be coated with an agent that increases the wetability of the tubing, preventing retention of urine within the tubing.

As described above and herein, any of the combinations of these features (e.g., expandable or self-expanding containers, expandable tubing, pumps, meters, or the like), may be used in any combination or sub-combination to form a multi-functional urine collection device. Further, any of these components may be part of a urine collection system and may be used to collect and/or dispose of urine from a subject in need thereof.

These and other embodiments, features, and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 1A and 1B show perspective and side views, respectively, of a urine collection system as described herein.

FIGS. 2A and 2B show a urine collection device having an expandable container as described herein.

FIGS. 3A and 3B show another variation of a urine collection device as described herein.

DETAILED DESCRIPTION OF THE PREFERRED EMBODIMENTS

Figure 4:
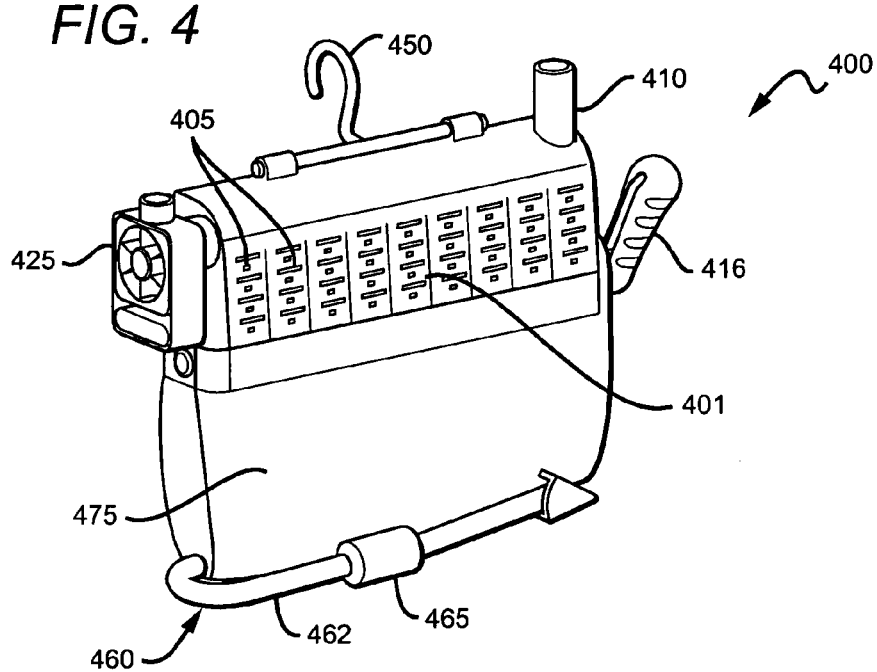
FIG. 4 shows a perspective view of a portion of a urine collection device as described herein.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing embodiments of the invention, it is to be understood that unless otherwise indicated, this invention need not be limited to applications in humans. As one of skill in the art would appreciate, variations of the invention may be applied to other mammals as well. Moreover, it should be understood that embodiments of the present invention may be applied in combination with any appropriate catheter, including but not limited to Foley catheters. Urinary catheters may include any tube or tube-like structure that provides access to the bladder. Urine collection systems and devices, as described herein, may be used to collect urine from any subject in need thereof. A subject may include any appropriate user, including a medical patient. It must also be noted that, as used in this specification and the appended claims, the singular forms "a," "an" and "the" include plural referents unless the context clearly dictates otherwise. Thus, for example, the term "a catheter" is intended to mean a single catheter or a combination of catheters, "a fluid" is intended to mean one or more fluids, or a mixture thereof.

The collection devices described herein may include a container having a receptacle for holding urine, at least one inlet or opening into the receptacle through which urine may pass, and tubing forming a fluid connection between the receptacle and the catheter through which urine may pass. As described further below, a urine collection device may also include an expandable container, a meter for measuring at least one parameter from a subject's urine, extendable tubing, and a pump to help move urine from the tubing and into the receptacle. Additional components, particularly those concerned with preventing or reducing leakage and spilling of urine from the urine collection system, and preventing pooling of urine in the catheter and tubing are also described.

Expandable Containers

Any appropriate container may be used as part of the urine collection devices and systems described herein. In particular, the urine collection device may include an expandable container for connecting to a catheter and collecting urine therefrom. An expandable container may be any container having a receptacle that has an "open" or expanded configuration, a "closed" or collapsed configuration, and a bias for converting the container from the closed to the open configuration (or from the open to the closed configuration). Thus, the interior volume (e.g., the volume of the receptacle) of the expandable container may increase or decrease depending on the configuration of the expandable container. The expandable container may assume any configuration between fully expanded and collapsed.

The expandable container may be fully or partially expanded during use. In some variations, the expandable container can be completely collapsed, so that there is little, if any open volume into which urine can drain. Furthermore, collapsed containers can be more easily stored or disposed. In some variations, the expandable container can be only partially collapsed, leaving some residual volume. Filling a container having an open volume (such as an expandable container that is fully or partially expanded) is typically easier than filling a closed volume. For example, the filling pressure required to fill an open container is less than the filling pressure required to fill a closed container, because force must be used to open the closed container as it is being filled. Thus, the filling pressure (force) must be sufficient to open the container, otherwise fluid will not enter the container. In a urinary collection system, this may mean that urine will stand within the tubing connecting the urinary collection container and the catheter, or reflux back towards the catheter. Thus, an expandable container may include a bias to automatically open (or close) the container.

In general, a bias tends to automatically open or close an expandable container. For example, a bias may act on the walls of the expandable container to force them apart and thereby expand the expandable container. An expandable container may have either hard walls, soft walls, or a combination of hard and soft walls. One or more biases may be attached to one or more of the walls of the expandable container to apply force to open or close the container. For example, a collapsible container may be made of layers of PVC material welded along an edge, and a bias, such as a leaf spring, may be connected (e.g., attached to the walls or contained within the walls) thereto. Without a bias, the container must be opened manually before its use (e.g., by pulling the edges away from each other). A bias typically automatically opens the expandable container, and keeps the container in the open configuration. Any appropriate bias may be used to apply force to convert the expandable container between a closed and an open configuration. For example, a bias may include a biasing element, such as a mechanical bias (e.g., a spring, elastic, etc.), a pneumatic bias (e.g., applying air pressure to open the expandable container), an electrical bias (e.g., a magnet, or motorized biasing element), or the like, or any combination thereof.

For example, a biasing element can be a spring. In some variations, the bias is a compression/torsion spring. In one variation, the bias is a leaf spring that applies force to open or expand an expandable container. Such mechanical biases may be made from any appropriate material, including elastic, or shape-memory materials. For example, a bias may be made of metals (e.g., steel, carbon, nickel, copper, titanium, etc.), including alloys (e.g., Nickel-Titanium Alloy, etc.), polymers (e.g., plastics, rubbers, etc.), or any other appropriate material or combination of materials. In some variations, the bias may be made of a material that is capable of withstanding standard sterilization methods and retaining its function.

A bias may be a separate part of an expandable container, or it may be integral to the container. For example, the walls, edges, or other regions of the expandable container may act as a bias. In one variation, the container includes a material that can be deformed from a relaxed configuration (in which the expandable container is expanded), into a compressed configuration (in which the expandable container is closed). In one embodiment, the walls include a material having a shape memory. Releasing the expandable container from the compressed configuration allows the container (e.g., the walls of the container) to return to the relaxed configuration, opening the container. Thus, a bias can automatically open an expandable container. In some variations, the expandable container may be held or secured in a configuration (e.g., compressed or expanded) by a holdfast.

Any appropriate holdfast may be used to maintain the position of the expandable container. For example, a holdfast may include a latch, a strap, a tie, a button, a snap, a lock, an adhesive, a clamp, etc. In some variations, a holdfast prevents the expandable container from expanding when in the collapsed state. In some variations, the holdfast prevents the expandable container from collapsing when in the expanded state. Thus, a holdfast can be used to hold the expandable container in an open configuration or a closed configuration. The holdfast may be manually secured by a user, or automatically secured. For example, the user can release a holdfast holding the expandable container collapsed. This allows the expandable container to expand into an open configuration so that urine can readily fill the inner receptacle volume. In another variation, the same holdfast, or a different holdfast can be used to hold the expandable container in the open configuration so that it does not collapse during use.

The holdfast can attach to the expandable container (e.g., the walls or sides of the expandable container), or to any other region of the urine collection device, such as the bias). For example, the holdfast can include a member (e.g., a beam) that attaches between two or more walls of the expandable container, preventing them from moving relative to each other. In some variations, the expandable container is locked or held in the collapsed state by packing materials (e.g., a box, a wrapper, etc.).

The expandable container may be made of any appropriate material capable of retaining urine, including but not limited to: rubbers (e.g., natural rubbers, halogen-free diene rubbers, hydrogenation products of halogen-free diene rubbers, acrylic rubbers, epichlorohydrin rubbers, olefin rubbers, halogen-containing rubbers, silicone rubbers, pure rubbers, fluorinated rubbers, and fluorinated blends, mixtures of rubbers and polymers, etc.), plastics (polyolefins, such as polyethylenes, plastomers, polypropylenes, chlorinated vinyl resins such as polyvinyl chloride, polyurethanes, ethylene-vinyl acetates, polyesters, nylon, etc.), papers (e.g., cellulose, etc.) or combinations of materials. Furthermore, the expandable container can include combinations of materials (e.g., layers, regions, etc.), and different materials in the combination can have different properties.

In one embodiment, the inside of the expandable container includes a receptacle that is used to store urine when the expandable container is in the expanded state. Thus, the inside of the expandable container can include a liquid-proof material or a material that is coated to prevent leakage or damage from the urine, such as a hydrophobic material (e.g., waxes, plastics, etc.). In some variations, the expandable container is modular. For example, the receptacle region of the expandable container may be separate from the outer surface of the expandable container. Thus, the expandable container can include a combination of materials having different properties. In some variations, the expandable container includes a framework (e.g., a collapsible/expandable framework) to which the receptacle region is attached.

The expandable container can include a flexible material, a rigid material, or a combination of flexible and rigid materials. For example, the walls of the expandable container can include a durable, stiff material so that the expandable container can support its own weight. In some variations, the expandable container includes a flexible material to facilitate collapse thereof to a very small profile (e.g., for storage or packaging). In one variation, the expandable container includes a material that has a relatively high toughness. Thus, the container can be durable enough to withstand multiple cycles of opening and closing, while also having a relatively high puncture resistance.

The expandable container can include a disposable material, and all or a part of the expandable container can be disposed of after collecting urine. For example, the expandable container can include a "flushable" material that can be disposed of in a septic system. The expandable material can therefore be made of a material that degrades or decomposes over time, or after contact with a catalyst. In some variations, the expandable container is reusable, while the receptacle region is disposable. Any portion of the expandable container can be coated, embedded or treated with a material to provide beneficial properties. For example, the expandable container can be coated with odor eliminating materials, antibacterial materials, antiseptic materials, perfumes, colorants, etc.

The expandable container can include any appropriate shape in either the expanded or collapsed state. For example, the expandable container can include a series of "nested" shapes, which telescope out from the collapsed to the expanded shape. The expandable container can also include a functional shape, such as a shape having stability when standing in the expanded state so that it can rest upright, allowing filling from an inlet near the top of the device. For example, the expandable container can include a bottom region that is flat. The expandable container can also include hooks or attachment sites for hangers, stands, and the like.

In some variations, the expandable container is configured to have a wide base region, so that urine may be stored in the receptacle away from the inlet. Thus, as urine fills the expandable container, it is prevented from blocking the inlet, flowing backwards, and/or leaking. The expandable container can also be shaped or adapted to connect with (or include) a meter system or empting container or attachment, or any other appropriate device, as described further below. The expandable container can be calibrated, or can be formed to hold a specified amount of urine. Examples of different types and shapes of expandable containers are illustrated in the figures and described herein.

FIG. 1 shows an example of a urine collection device 100 having an expandable container 101 forming a receptacle. The expandable container 101 is a telescoping-type container which is shown with three segments that expand outward to form an open inner volume into which urine can flow. The expandable container 101 includes a bias (not shown) which automatically expands the container. Before use, the container may be collapsed so that the segments fit into each other, reducing the inner volume, as well as the overall profile of the urine collection device. The expandable container shown in FIG. 1 has somewhat rigid walls which maintain their shape without additional support. The expandable container 101 is also shown as transparent, allowing the level of fluid in the container to be visually monitored. The container (or region of the container) can be any color. In some variations, only a portion of the container is transparent (or translucent). In some variations, the container is opaque. The level of urine within the container can be monitored in any appropriate manner, including visually, electronically, or the like. For example, the expandable container can include a sensor that detects the level of urine within the receptacle, so that it may be indicated.

The example of a urine collection device shown in FIG. 1 includes other features that may be included in variations of a multi-function urine collection system, including an outlet or drain 105 that connects to a flushable pouch 107 or other removal system, extendible tubing 110 connecting to the catheter (shown as a Foley catheter 120), and a fluid transport pump 115 to help move urine from the tubing into the expandable container 101. A monitor or meter 130 can also be used to measure and/or transport or record one or more characteristics of the urine (or of the subject). The urine collection device can also include a hook 125, a stand, or any other appropriate attachment or securement region. The urine collection device shown in FIG. 1 includes a hook 125 attached to the back side of the expandable container; however, this attachment can be connected anywhere on the urine collection device. In some variations, a strap (e.g., a belt, a tie, etc.) may be used instead, or in addition to, a hook or other type of attachment.

FIGS. 2A and 2B show another variation of an expandable container 200. This variation includes a spring (not shown) that pushes the opposing sides of the expandable container apart, as shown in FIG. 2A. The spring may also hold the unit open. In some variations, the maximum open volume is limited by the size of the expandable container and not the leaf spring. For example, the maximum open volume may be achieved before the spring is completely relaxed because the shape and size of the expandable container limits the size to which the container can be opened. In FIGS. 2A and 2B, the urine collection device includes a meter 210 having a measurement region that is calibrated into which urine enters from the tubing 220 before entering into the receptacle part of the container. Thus, the amount of urine entering the device over time may be monitored. In some variations, there is a port connecting the meter to the receptacle of the urine collection device that may be opened or closed to permit or limit the flow of urine from the meter into the collection receptacle. In FIGS. 2A and 2B, the urine collection device is shown having a horizontal orientation, although in operation, this urine collection device may be oriented vertically, so that gravity may assist the flow of urine into the meter, collection device, and/or the outlet 205.

FIG. 2B shows the urine collection device of FIG. 2A in a collapsed configuration. Pressure (as from a hand, or a locking device) is applied and maintained to compress the expandable container. The walls of the expandable container in FIGS. 2A and 2B are flexible, so that they may be readily collapsed as pressure is applied against the bias. Thus, this urine collection device may be stored or packaged in a low-profile configuration.

Another variation of a collapsible chamber 301 for a urine collection system 300 is shown in FIGS. 3A and 3B. In this example, the bias expands the expandable container by pushing against at least two of the walls (here, two opposing walls) of the collapsible chamber 301. The bias includes a compression spring (not shown) and the collapsible chamber includes a three piece construction. In one variation, two of the walls (e.g., two of the facing walls) are rigid or semi-rigid, and the connecting sides (or continuous side) include a flexible material, so that the inner volume may be readily collapsed and expanded. The collapsible chamber is shown fully expanded in FIG. 3A. FIGS. 3A and 3B also shows additional features that may be included on any of the urine collection devices and systems described herein, including a first meter (shown as an electronic meter 320), a second (volume indicating) meter 330, a fluid transport pump 340, and an outlet port 350 for connection to a disposable pouch 360 (as shown in FIG. 3B) from which urine can be emptied from the expandable container.

As shown in FIGS. 1-2B, fluid held in the inner volume of the expandable container (the receptacle) can be drained by any appropriate method. For example, the expandable container can include a drain at the base (or any other appropriate location) through which urine can be emptied from the container. Urine can be drained directly into a waste container (e.g., a waste container, a disposable bag or pouch, a toilet, etc.), or into an intermediary holding and/or transport device (e.g., a transfer container, or the like). The drain or outlet may be any appropriate outlet to allow or encourage urine to drain from the collection device. In some variations, the urine collection device includes an outlet having a controllable, outlet port that permits fluid to flow from the urine collection device without spilling or leaking. For example, the urine collection device may include an interlocking mechanism that does not permit urine to flow from the collecting (e.g., expandable) container until a sealed connection has been made with an intermediary holding/transport device, or unless an override is triggered. The outlet may also include a one-way port, to prevent backflow into the receptacle.

Returning to FIG. 1, the expandable container 101 is shown having an outlet 105 at the base of the urine collection device 100. The outlet includes a tube or sheath surrounding a valve. The sheath may protect the valve, and help connect and/or seal the valve to an attachment on a waste container (e.g., a disposable pouch 107, as shown in FIG. 1). The outlet can also include a mating region for mating with a waste container. Thus, the useful lifetime of a urine collection device, and particularly the container portion of the urine collection device, can be extended by allowing the device to be drained. Draining the urine collection device may also make disposal or urine more sanitary.

In some variations, the urine collection system (including urine collection systems that do not include an expandable container, as described further below) are closed systems, so that urine does not leak, or otherwise leave the urine collection system, thereby minimizing contact with urine during operation and emptying of the urine collection system. In some variations, the system is an entirely closed system. For example, the system may not include an outlet port. In some variations, the urine collection system includes an outlet having a check valve interface for coupling to a receiving device (e.g., a flushable pouch or other transfer container). The flushable pouch can include a material that is disposable (e.g., biodegradable), as previously described. Thus, the flushable pouch can be disposed of in any appropriate fashion. In some variations the flushable pouch can be flushed down a toilet. In some variations, the flushable pouch is disposed of using other waste-disposal techniques (e.g., solid waste disposal, non-septic waste disposal, etc.). The check valve interface can include any appropriate valve that mates and opens with an appropriate (e.g., matching) partner to allow fluid to flow through the valve.

As described, one or more biases may be used to expand an expandable container into an open configuration so that urine may readily flow into the urine collection volume. Thus, the bias may provide force necessary to open the expandable container. Part of the forces overcome by the bias may be the internal pressure in the urine collection system, including the expandable container. For example, the air pressure within the urine collection device (particularly the expandable container) can be regulated. A pump may be provided to draw urine through the tubing and into the receptacle of the urine collection device, as described below. Furthermore, when the expandable container is expanded from a collapsed state, pressure within the urine collection device may be lower than external air pressure. The urine collection device can also include one or more air inlet and/or outlet valves that may either passively or actively regulate the air pressure within the urine collection device.

Air inlet valves include any appropriate valve for equalizing air pressure within the urine collection device with external air pressure. In some variations the air inlet valve is configured to allow only air (not liquid) to flow from within the urine collection device. For example, the air inlet valve may be placed near or above the top of the urine collection device so that urine cannot readily enter it. In some variations, the air inlet valve includes a one-way valve, preventing urine from exiting the urine collection device through the air inlet valve. For example, the air inlet valve may include a ball valve, a flap valve, a membrane valve, or any other appropriate valve. In some variation, the inlet valve is also an outlet valve. In other variations, a separate outlet valve may be used. The air inlet valve may be actively regulated. For example, air may be allowed to enter or leave the urine collection system only during certain times (e.g., when expanding the expandable container, or when pumping fluid from the tubing into the receptacle, etc.). Thus, the air inlet valve may be regulated by computer, mechanical, or manual control, and control may be linked to other functions or devices of the urine collection device (e.g., a pump, a meter, etc.).

In one variation, the air inlet valve includes a lock to maintain the position of the expandable container, as described above. Thus, when the collapsible container is in the collapsed state, the air inlet valve is closed, and external air cannot otherwise enter the collapsible container. Opening the air inlet valve allows the bias to force open the collapsible container and can equilibrate the pressure difference between the inside and the outside of the collapsible container.

An expandable container can be compressed and packaged for later use. When the packaging is removed, the container can automatically spring open to provide a volume (e.g., 1, liter, 2 liters, etc.) into which urine can be drained. For example, a package may contain a lock, clamp, or other component that applies an outer force to the sides of a container, keeping the container closed despite a bias force tending to expand the container. The container can be automatically opened after removing the expandable container from the package by a bias, such as a leaf spring.

In operation, a urine collection device with an expandable container can be used to collect urine from a subject, particularly a subject having a urinary catheter. The urine collection device may be sterilized, or packaged clean or sterile. Thus, the urine collection device (or system) may be removed from the clean or sterile packaging immediately before use, and prepared for connection to the subject. The expandable container can thus be expanded by the bias prior to connection to the subject from a contracted position into an expanded position. The bias automatically opens the expandable container, generally without needing to be manually expanded or forced open by the flow of urine into the receptacle. The urine collection device can then be connected (e.g., via tubing) to a subject wearing a urinary catheter, or to urinary catheter to be worn by a subject. In some variations, the expandable container is expanded after connection to the subject. Once properly connected, urine may drain from the subject's bladder into the receptacle of the urine collection device.

All of the urine drainage and disposal devices, meters, tubing, inlets, outlets, ports, and the methods and techniques described herein can be used with any appropriate urine collection system, and are not limited to urine collection systems having expandable containers.

Meter

A urine collection device or system can include a meter for measuring at least one characteristic from urine (e.g., flow rate, volume, temperature, salinity, pH, concentration of materials, etc.). Any appropriate meter may be used. A meter can include a measurement region, to measure a characteristic from the urine, and a release to control the release of urine from the meter into the receptacle of the urine collection device. The meter may be configured so that urine enters (or passes through) the meter before entering the receptacle region of the urine collection device.

In some variations, the meter is configured to measure the volume of urine from a subject to whom the urine collection system is attached. For example, the urine collection device can include a meter having an inner measurement region that is calibrated by volume. Urine passes from the tubing connecting the urine collection system to the urinary catheter into the calibrated measurement region of the meter. The urine can be retained in the calibrated measurement region before being emptied into a receptacle region to allow the amount of urine to read, measured, and/or stored. In some variations, the meter can include a series of calibrated volumes that are linked together so that, once one calibrated volume is full, the next calibrated volume then fills.

For example, urine can flow into meter with a volume that is divided into smaller calibrated volumes. As urine enters the meter, it passes into a first chamber which holds a first volume of urine (e.g., 5 ml, 10 ml, 25 ml, 50 ml, 100 ml, etc.). Once the volume of urine in the first chamber exceeds the capacity of the first volume, urine spills over into a second volume that is also calibrated to hold a known volume of urine (e.g., 5 ml, 10 ml, 25 ml, 50 ml, 100 ml, etc.), and so on. As the amount of urine exceeds each progressive volume, it spills into another chamber that is also calibrated to hold a known amount of urine. Any number of chambers may therefore be linked together in this manner, allowing measurement of the volume of urine from the subject. Furthermore, the calibrated chambers may be marked to indicated sub-volumes (e.g., 1 ml, 5 ml, 10 ml, etc.) that can be read to indicate volume more precisely, particularly when the last volume holding urine is not completely filled. Each calibrated volume may hold the same amount, or may hold different amounts.

In some variations, the meter measurement region is transparent, translucent, or otherwise allows an observer to view urine within the measurement region. This is particularly useful in variations in which the measurement region is calibrated so that the volume of urine within the meter can be observed directly. Thus, the amount of urine from within the calibrated measurement region can be visually determined. In some variations, the meter includes markings indicating the volume contained within the meter region, or the different sub-regions of the meter. After observing or recording the amount of urine in the meter, urine can be released from the urine collection device into the receptacle, which may hold a large volume of urine. In some variations, the meter includes a meter release for opening or closing ports connecting the meter and the receptacle region of the urine collection device.

The meter can also determine the flow rate of urine from the catheter. Thus, the meter can include a sensor for detecting the flow rate of urine. The meter can determine the amount of urine entering the urine collection device over a known time by including a timer with a calibrated measurement region (e.g., to approximate the rate of urine entering the measurement region). In some variations, the meter calculates the flow rate. In general, a meter can include one or more electronic components for sensing, calculating, displaying, transmitting, or storing one or more characteristics of the subject's urine, such as flow rate.

The meter may measure any appropriate characteristic. In addition to urine volume and flow rate, the meter may measure the temperature of the urine, the pH, the chemical composition (e.g., concentration or presence of urea, ions, salts, hormones, proteins, lipids, etc.), osmotic pressure, or any other characteristic. For example, the meter may include one or more sensors (e.g., electrical, chemical, chemoelectric, etc.) to help determine one or more characteristic. The meter may be linked to a controller, such as a computer, or other electronic device, to detect, store, transmit, analyze and display the urine characteristic(s) that are detected. In some variations, the meter may be remotely connected to a controller or storage device.

The inside of the meter (the region that contacts the urine) may be linked with the receptacle region of the urinary collection device thorough one or more openings that can be opened or shut to allow urine to pass from within the meter into the receptacle region. For example, the meter can include a plurality of ports through which urine can pass from the meter into the receptacle. In some variations, urine passes directly through the meter without stopping; however, in other variations, urine can be retained within the meter to allow measurement therefrom. Thus, the ports linking the meter and the receptacle region may be opened or closed (or partially closed) to release urine from the meter into the receptacle. Urine may be released from the meter by a meter release control (e.g., a button, lever, etc.). The meter release may open some (or all) of the ports to empty the meter. This can reset the meter and allow it to make further measurements. By opening a plurality of ports, the meter can be very quickly reset, since the volume of the measurement region of the meter can be emptied in parallel. Rapid resetting of the meter may be particularly advantageous during a rapid flow rate.

In some variations, the meter release is a manual release, such as a button, lever, handle, or toggle, or other trigger that releases urine from the meter into the receptacle. Operation of the meter release may be partially or completely automated. For example, the meter release can include an automatic return so that triggering the meter release holds the openings between the meter and the receptacle open for some predetermined period of time (or until the meter is completely drained), and then closes them, resetting the meter release. For example, the meter release may include a spring to close the meter release after emptying the meter. Operation of the meter release can be triggered when the meter is filled to some preset or predetermined level. For example, the meter can include a sensor detecting urine in one or more of the calibrated meter chambers, and thereby trigger emptying of the meter. In some variations, the sensor is a mechanical sensor (e.g., the weight of urine in the chamber triggers the release), or an electrical sensor.

A meter may be used with any appropriate urine collection device or system. In some variations, the receptacle region includes an expandable container as described above. Examples of meters appropriate for urine collection system may be found in the figures, including FIG. 4. In FIG. 4, the urine collection device 400 includes a meter 401 configured to measure urine volume. This variation of a meter 401 includes a series of serially-connected calibrated chambers 405 that have calibration marks on the transparent surface of the meter to indicate the volume of urine held in each chamber. The inlet 410 links the inside of the meter to tubing that can connect to a urinary catheter. Thus, urine can flow into the meter from the catheter. The urine first fills up the calibrated chamber of the meter nearest to the inlet (shown here at the far right side of the meter). Once this first chamber is filled, urine spills over and begins to fill the adjacent calibrated chamber. The top part of each chamber of the meter is connected, allowing urine to spill from one chamber to the next, as described above.

In FIG. 4, the meter release 416 includes a handle or lever that can be used to drain the meter into the receptacle. The receptacle is shown as a collapsible bag 475. In some variations, this receptacle includes an expandable container having a bias that automatically opens the receptacle to receive urine. The urinary collection device shown in FIG. 4 also includes a pump 425 that can draw urine from the tubing and into the meter and receptacle. The pump is located across from the inlet port 410. An outlet 460 may be connected to the receptacle so that urine may be emptied, as previously described. In FIG. 4, the outlet includes tubing 462 and an outlet valve 465 that may be connected to an emptying device such as a transfer container or a disposable (e.g., flushable) bag. FIG. 4 also illustrates a hook 450 that can be used to attach the urine collection device to the bed, a stand, or any other appropriate structure. Thus, the urine collection device may be oriented so that urine flows (by gravity and/or the pump) into the meter and receptacle from the catheter. As described above, any appropriate attachment may be used in addition to (or instead of) the hook shown.

Figure 5A:
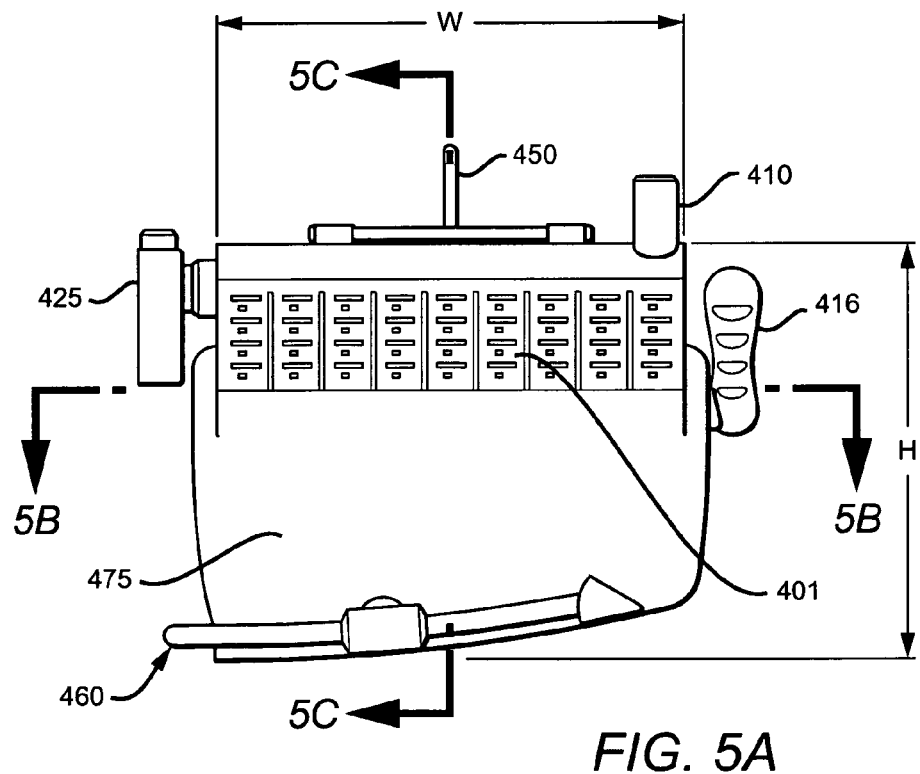
FIG. 5A shows a front view of a urine collection device similar to that shown in FIG. 4.
Figure 5B:
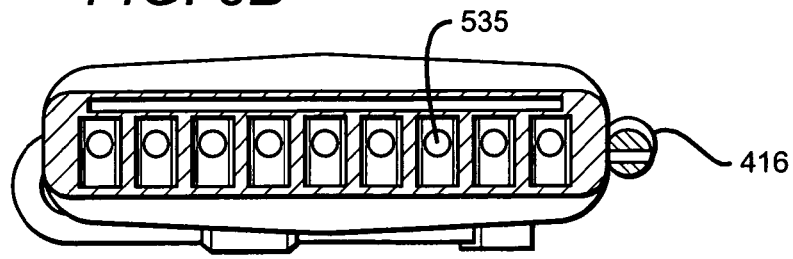
FIGS. 5B and 5C show transverse and sagittal sections, respectively, through the urine collection device shown in FIG. 5A.
Figure 5C:
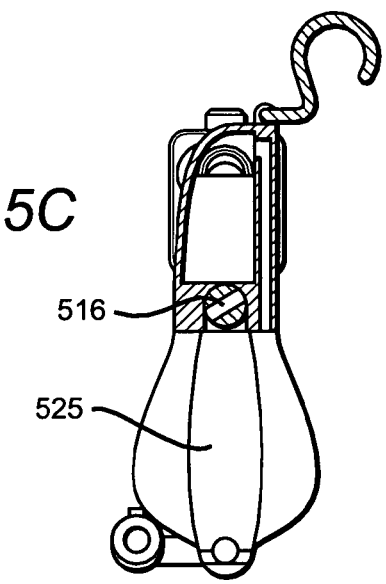
Figure 5D:
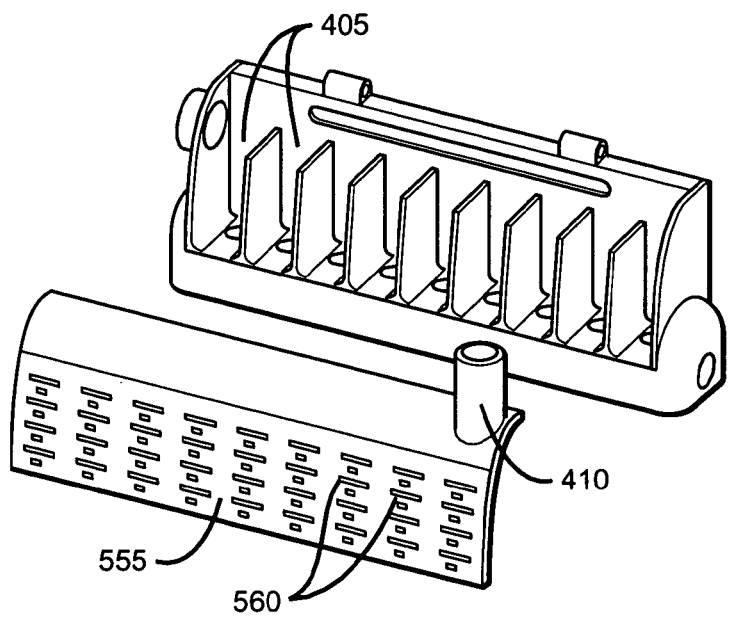
FIG. 5D shows an exploded view of one region of the urine collections device shown in FIG. 5A.

FIGS. 5A to 5D show different views of a urine collection device having a meter similar to the urine collection device shown in FIG. 4. FIG. 5A shows a frontal view of a urine collection device. Features such as those already described from FIG. 4 are similarly labeled in FIG. 5A to 5C, such as the meter 401, meter release 416, pump 425, outlet 460, inlet 410, receptacle 475, and hook 450. FIG. 5A also indicates relative dimensions of this example of a urine collection device. In FIG. 5A, section line B-B indicates a transverse section though the meter region of the urine collection device, and is shown in FIG. 5B. Section line C-C indicates a sagittal section through the urine collection device, and is shown in FIG. 5C. Finally, FIG. 5D shows an exploded perspective view of the meter of FIGS. 5A to 5C.

The transverse section through the meter in FIG. 5B shows a plurality of openings (or ports) 535 connecting the meter and the receptacle portions of the device. As described above, these ports may be blocked and/or opened by a meter release, to control emptying of urine from the meter. In FIGS. 5A-5D, the meter release is a valve 416 (e.g., an emptying valve) that may be manually pulled to empty urine in the meter into the receptacle. The valve may also be manually returned to the closed position. The operation of this simple example of a meter release is also illustrated in the sagittal section shown in FIG. 5C.

The meter release shown in FIGS. 5A to 5D includes a rotatable rod having passages therethrough. The release may be opened, allowing urine to empty from the meter into the receptacle by moving the handle 416 (or emptying valve) so that the passages through the rod line up with the openings in the meter 535 and the openings into the receptacle, so that urine may flow between the two. In FIG. 5C, a cross-section through the meter release 516 shows the meter release in the closed position, preventing the flow of urine into the receptacle from the meter.

In FIG. 5D, the exploded perspective view shows the construction of one variation of a meter, having serially arranged and calibrated regions for holding urine. In FIG. 5D, the outer transparent cover 555 of the meter region has been removed, revealing the inside of the meter. Thus, it is apparent that the upper region of the each of the calibrated regions 405 is open so that urine may cascade from one region into the next region as it enters the meter from the inlet 410 and fills up each calibrated region. The meter cover 555 is at least partially transparent, so that urine may be viewed through the cover. Furthermore, the cover includes markings 560 indicating filling volumes. These markings may be labeled so that an observer can readily measure a volume of urine held in the meter.

Figure 6:
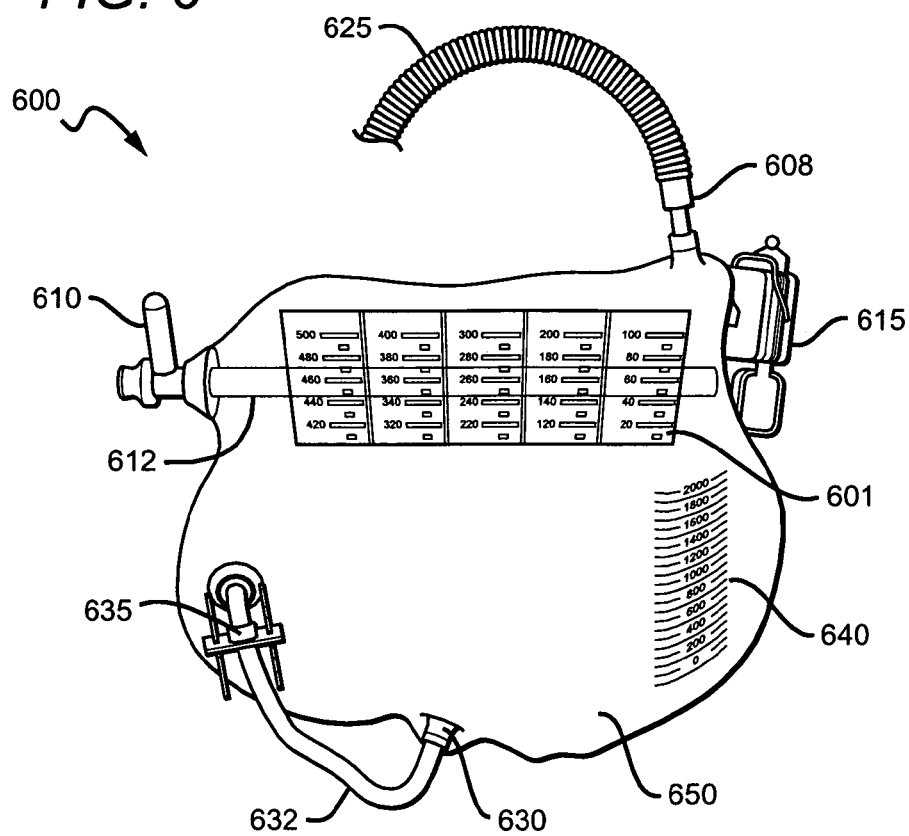
FIG. 6 is a perspective view of another urine collection system as described herein.

Another variation of a meter that is part of a urine collection system 600 is shown in FIG. 6. In FIG. 6, the meter 601 is calibrated and labeled to show the volume of urine entering through the inlet 608. A meter release 612, including an emptying lever 610, may be triggered to empty urine from the meter into the receptacle 650, or drainage bag. In addition to the meter 601, the receptacle 650 also includes markings 640 (or calibrations) that may provide a rough or approximate estimate of the volume of urine within the receptacle. The receptacle also includes an outlet or drain 630 having drainage tubing 632 and an outlet valve 635. In some versions, this outlet valve includes a duckbill valve, or other secure valve to prevent the leakage or release of urine unless the outlet valve is engaged with a disposal device. A pump 615 is also included in order to draw urine from the tubing 625 into the meter 601 and receptacle 640.

Figure 7:
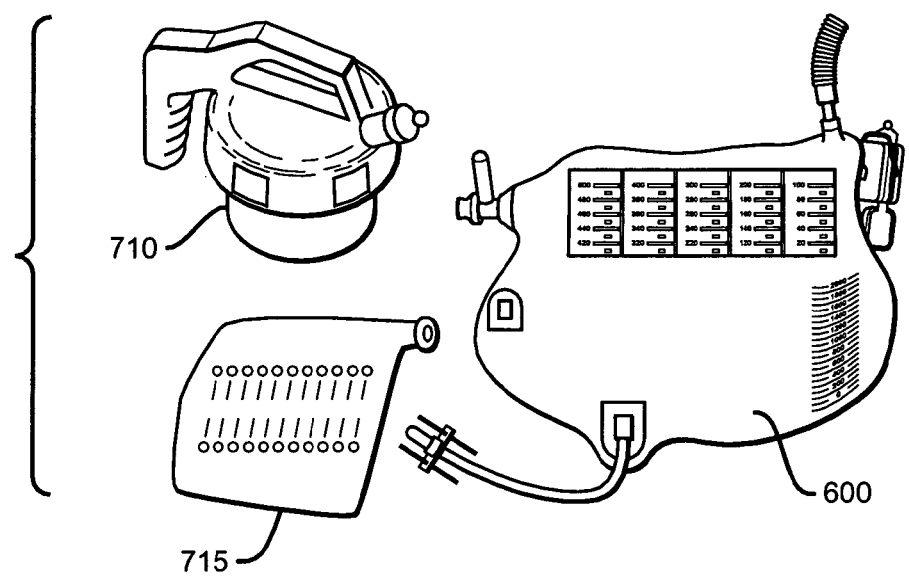
FIG. 7 is another perspective view of the urine collection system as shown in FIG. 6, including additional components.

FIG. 7 illustrates a system for collecting urine 600 including a meter, as described. FIG. 7 also includes additional components, such as a transfer container 710, and flushable bags 715. Either the transfer container 710 or the flushable bag 715 may be attached to the outlet valve 635 to empty urine from the receptacle for disposal.

In operation, a meter may measure any appropriate characteristic of urine, such as volume, flow rate, chemical composition, etc. The urinary collection devices described herein may be attached to a urinary catheter (e.g., a Foley catheter) so that urine may flow into the urinary collection device, particularly the meter region of the urinary collection device.

The characteristic to be measured or monitored may depend up on the meter (or meters) of the urine collection device. Although the examples of meters described herein describe measurement of urine volume, any appropriate meter may be used, including, but not limited, to meters for measuring flow, temperature, pH, chemical composition, etc. More than one meter may be used, and multifunctional meters may be used. Urine may be held by the meter for measurement and later emptied into the receptacle, or measurements may be made from the urine as it passes through (or by) a meter.

In general, the flow of urine from the subject (e.g., a catheter in a subject) into the urine collection system may be facilitated by actively moving urine through the system. In some variations, a pump may be used to move urine within at least a portion of the collection system.

Pump

A pump may be used as part of a urine collection device or system. A pump, and particularly a fluid transport pump, may help move urine within the fluid collection system so that urine can be collected in a receptacle of a urine collection system. For example, a pump may be used to move urine though tubing (e.g., connected to a catheter) and into a receptacle having to collect the urine as discussed above. Suitable receptacles that may be used with the urine collection devices include expandable containers (as described above) and non-expandable containers (e.g., bags, boxes, pouches, etc.).

Typically, urine is drained through tubing and into a receiving volume (e.g., a receptacle) by gravity. The tubing is rarely oriented completely "downhill" over the entire length of the tubing as it travels from the catheter to the bag. For example, a subject wearing a catheter may shift position, or the tubing may have to be coiled, and the tubing pathway may have regions where urine collects, rather than continuously emptying into the receiving volume. Thus, a pump may be included to move urine from the tubing and into the receiving volume of the urine collection device, such as a receptacle or a meter.

Any appropriate pump may be used. For example, the pump may operate by applying positive pressure (blowing) or negative pressure (suction). Example of different kinds of pumps that may be used include, but are not limited to: impeller pumps, gear pumps, finger pumps, diaphragm pumps, infusion pumps, peristaltic pumps, piston pumps, variable displacement pumps, rotary pumps, etc. The pump may be battery powered. The pump may be associated with one or more air inlet valve to prevent suction from entering a subject's catheter. For example, an appropriate air inlet (or outlet) valve may include a one-way valve or air inlet port located near the catheter/tubing interface (e.g., near one end of the tubing). In some variations, the urine collection system includes multiple air inlet/outlet valves to help regulate the pressure within the urine collection system.

The operation of the pump may be regulated. For example, the pump may be activated (turned on and/or off) either manually or automatically, or some combination thereof. The pump may be entirely manually operated so that the pump is turned on or off by a user. In some variations, the pump may include a timer so that it runs for some predetermined time period. In some variations, the pump is connected to a sensor that can control the operation of the pump. For example, the sensor may detect fluid within the tubing (or a region of the tubing, e.g., near the catheter), and may activate the pump. In some variations, the pump is controlled by a controller. The controller can include hardware, software, or any combination thereof, for controlling the operation of any portion of the urine collection system, such as the pump, meters, and other sensors, air inlet/outlet valves, etc.

The pump can be disposable or reusable. In some variations, the pump may be reused with non-reusable components of the urine collection system. For example, the collection tubing and receptacle portions of a urine collection system may be replaced but the same pump may be re-used. Likewise, other components of the urine collection system may be reusable or disposable (e.g., the sensors, etc.).

The pump may be located in any appropriate position of the urine collection system so that the pump will move urine through the tubing and into the receptacle to collect the urine. For example, the pump may be located near the receptacle, interfacing with the drainage tubing to move fluid down the tubing and into the receptacle. In some variations, the pump interfaces with the receptacle directly, and not the tubing. In variations where the pump increases pressure within the tubing, it may be beneficial to locate the pump near the junction of the catheter and the tubing so that pressure pushes the urine down the tubing and into the receptacle. The pump may also be adapted to apply only an acceptable range or pressures within the urine collection system. For example, the pump can include one or more governors to prevent applying to much pressure (positive or negative) within the urine collection system. Thus, the pump may automatically shut off if the load on the pump exceeds a threshold value.

Figure 8:
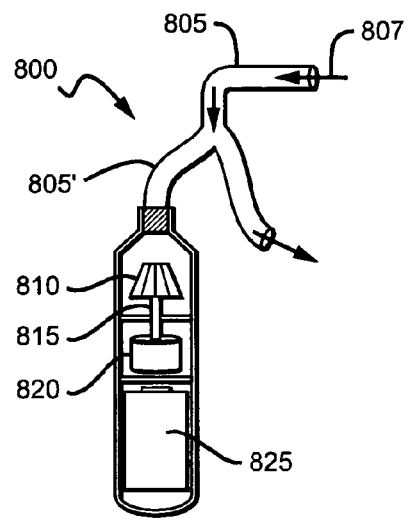
FIG. 8 shows a schematic illustration of a pump for use with a urine collection device, as described herein.

FIG. 8 shows one example of a pump that may be used with the urine collection system as described herein. FIG. 8 shows an impeller-type pump 800 that is connected to the tubing 805 through a branch tube 805'. In this example, the impeller pump includes an impeller blade 810 that is rotated on the axle 815 and driven by the motor 820. This pump is powered by a battery 825. In operation, rotation of the impeller blade draws a vacuum that pulls urine down the tubing 805 in the direction shown 807. As described above, any appropriate type of pump may be used to apply pressure and move urine down the tubing and into the receptacle, including pumps having displacement chambers, propellers, and diaphragms.

In some variations, the pump interfaces with the internal region of the urine collection system. Thus, at least a portion of the pump is continuous with the internal region of the urine collection system. In other variations, the pump remains completely external to the urine collection system. For example, the pump may be a peristaltic pump that operates on the tubing to move urine down the tubing and into the receptacle. In this example, the urine collection system also includes an air inlet port near the beginning of the tubing (e.g., near the tubing/catheter interface) in the receptacle (or near the tubing/receptacle interface). This prevents excessive pressure or vacuum from developing in other parts of the urine collection system (or the catheter). In operation, a pump may move fluid through tubing and into a receptacle. The pump may draw (e.g., by negative pressure or vacuum) or push (by positive pressure) fluid through the tubing. The pump may be activated when urine is present in the tubing and inactivated when urine is no longer in the tubing.

Other examples of urine collection systems having pumps are shown in FIGS. 1, 3A and 3B, 4, 5A, and 6. For example, in FIGS. 1, 3A and 3B, the pump 115, 340 is connected near the interface of the tubing and the receptacle (shown here as an expandable container). In FIGS. 4, 5A and 6, the pump 425 is connected to the meter 401, 601 attached to the receptacle 475, 650 so that a vacuum draws urine from the tubing into the meter and receptacle.

Extendable Tubing

As described above, a urine collection system typically includes tubing that can connect the subject (e.g., a catheter on a subject) to the receptacle into which urine is collected. Generally, tubing is draped down the bed and over the edge where it is attached to a collection receptacle (e.g., a urine collection bag). The receptacle is usually hung on one of the bed supports above the floor, and the difference in height between the catheter and the receptacle moves urine from the tubing and into the bag by gravity. Since most existing collection systems use tubing that is generally a single length for all sizes and bed lengths, excess tubing is often coiled either on the bed or around the collection bag, which can also create areas where urine can pool.

In some variations of the urine collection devices and systems described herein, extendable tubing that may be shortened or lengthened connects to the receptacle (e.g., an expandable container or a non-expandable container). In general, extendable tubing is flexible, adjustable tubing that can be lengthened and compressed, and will maintain or hold the length to which it is adjusted. Extendable tubing can include an inner (fluid-contacting) surface with a smooth inner wall surface. The inner surface may be made of an elastomeric material. The flexible tubing may also have an outer region (with an outer surface) that is adjustable by changing (e.g., expanding or contracting) the overall shape of the outer region.

In general, extendable tubing is any tubing that can change the length of the outer region of the extendable tubing between an elongated (or extended) length in which the extendable tubing is fully extended, and a compressed length, in which the outer surface is fully compressed. The tubing can be lengthened or shortened into any intermediate position between the elongated length and the compressed length. In some variations, the extendable tubing maintains the length to which it is adjusted, between (and including) the elongated and compressed lengths. Thus, the extendable tubing can be set to a length, and the tubing will stay at substantially that same length until it is readjusted. Typically, the outer region of the tubing (including the outer surface) provides the adjustability and support to the inner region (including the inner surface) providing a lumen with a continuous surface for contacting the urine.

In one variation, the outer region includes telescoping segments allowing the tubing to compresses or extend because one or more telescoping segments of the tubing slide within another segment of the outer surface of the extendable tubing. For example, the outer region of the extendable tubing can include at least two tubing segments that telescope between a compressed and an elongated length. Thus, the outer region of the extendable tubing can include a first tubing segment having an inner diameter substantially matched to the outer diameter of a second tubing segment, so that the second tubing segment is slideable within the first tubing segment. More than two segments may be connected in this way. For example, the extendable tubing can include a third tubing segment that may have the same inner diameter as the first tubing segment, so that the second tubing segment also slides within the third tubing segment.

In some variations, the outer and inner segments are size-matched so that, while one can slide within the other, they may hold their position unless some minimum force is applied to move them. Furthermore, the material comprising the segments may be selected to allow sliding, but also to maintain the position of the segments unless force is applied. Additional materials or structures may also be used to help maintain the position of the segments (and therefore the chosen length of the tubing). In some variations, a segment including an outer (telescoping) region includes a slider that prevents the telescoping segments from separating, and may help secure the extendable tubing at a selected length.

Figure 9A:
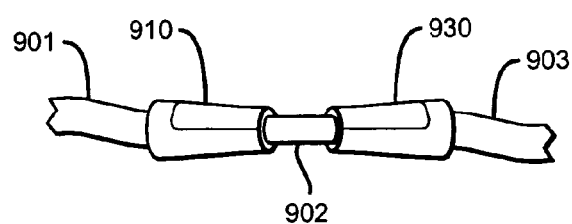
FIG. 9A shows a region of an extendible tubing for use with a urine collection device as described herein.
Figure 9B:
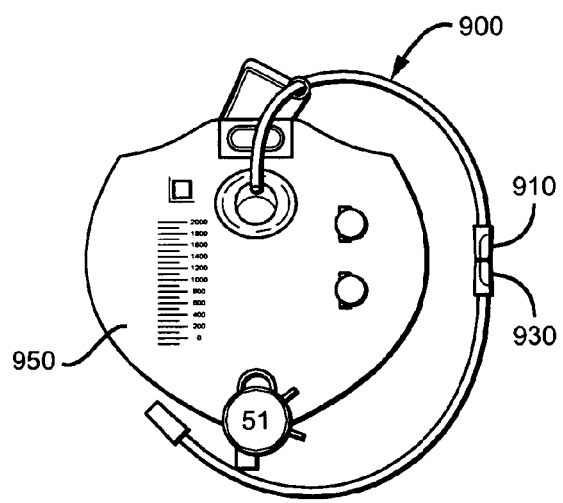
FIGS. 9B and 9C show a urine collection device having extendible tubing that is contracted and extended, respectively.
Figure 9C:
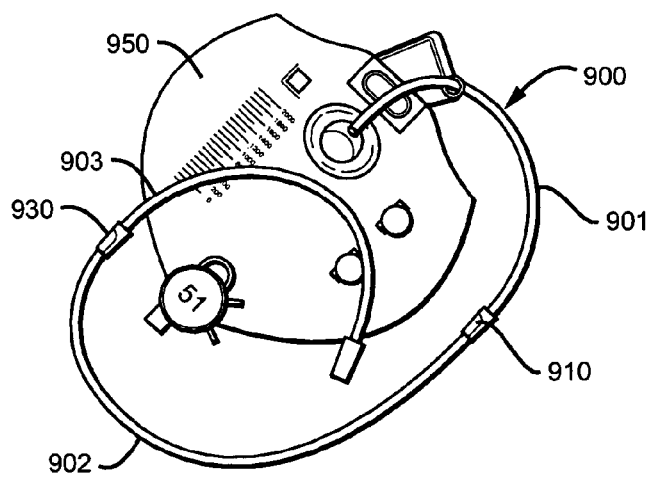

FIGS. 9A to 9C illustrate one variation of the extendable tubing having three telescoping segments forming the outer surface. In FIG. 9A, the junctions of all three segments of the extendable tubing are shown, illustrating an extendable tubing that in a compressed configuration. The first segment of the outer surface 901 is connected to a first slider 910 at one end and the second segment 902 slides through the slider 910 so that at least a portion of the second segment 902 slides within the lumen of the first segment 901. Similarly, the third segment 903 of the outer surface is attached to a second slider 930 through which the second segment 902 slides. Thus, the extendable tubing may be lengthened or shortened by telescoping the first and second and second and third segments with respect to each other to select a length for the tubing. FIGS. 9B and 9C show examples of urine collection devices having extendable tubing as shown in FIG. 9A.

In FIG. 9B, the extendable tubing 900 is shown in the fully compressed length. Both sliders 910, 920 abut each other, and the second segment 902 is completely within the first 901 and third 903 segments and the sliders. The extendable tubing 900 is also shown attached to a collection receptacle 950. In FIG. 9C, the extendable tubing 900 is in the fully elongated configuration. The second segment 902 is no longer completely within the first 901 and third 903 segments, and the second segment 902 is connected to the sliders 910, 930 linking the second segment to the first and third segments.

The extendable tubing can also include an inner surface forming a passage through the tubing. In one variation, the inner surface includes at least part of the inner surface of the segments forming the outer region. For example, in FIGS. 9A to 9C, the inner surface includes the inner surface of the first 901, second 902, and third 903 segments. In this example, the sliders 910, 930 seal the segments so that fluid may not leak from within the lumen of the extendable tubing. The inner surface in this example is not completely smooth, as there may be discontinuities at the edges of the second segment in the inner diameter.

In some variations, the inner surface is not formed from the outer region forming the outer surface. For example, the inner surface may be a lumen formed by another tube within the lumen of the outer region. The inner surface can include a single continuous wall, thereby preventing leaks and irregular regions, through which urine may leak, as well as small cavities or chambers where urine may be retained. In some variations, the inner surface includes an elastomeric material that can collapse or stretch as the expandable tubing is lengthened or shortened. For example, the inner surface can include a polymeric or rubber material formed into a tube. The inner surface may be attached to the structure (e.g., segments) forming the outer region in any appropriate position. For example, the inner surface may be anchored only at the ends of the tubing to the segments forming the outer surface, or at different points between the ends of the tubing.

Extendible tubing is not limited to tubing having an outer region that is telescoping. The outer region may change between an elongated length and a collapsed length in any appropriate fashion. For example, the outer surface may lengthen or shorten by expanding or contracting in an accordion fashion. Alternatively, the outer surface may extend or contract by changing diameter. FIGS. 2 and 6 show examples of a urine collection device and system having extendable tubing 220, 625 that lengthens and shortens accordion-style. For example, in FIG. 6, the extendable tubing 625 includes an outer region having circular ridges (accordion folds). The angle forming the ridges of the outer region of the tubing may be made bigger (e.g. up to 180 degrees) or smaller (down to almost 0 degrees) over some, or all, of the length of the tubing in order to lengthen or shorten, respectively, the outer region and therefore the length of the extendable tubing. The size and number of the ridges may help determine how extendable this variation of the extendable tubing is. Although the extendable tubing shown herein is substantially round in cross-section (e.g., cylindrical tubing), the extendable tubing may have any appropriate cross-section. For example, the tubing may have a square cross-section, a triangular cross-section, or a cross-section having any polygonal shape.

In operation, the tubing may be attached to a urine collection device (such a receptacle for holding urine) and/or a catheter. The tubing may also be part of a urine collection system. The tubing may be extended or contracted. For example, the tubing may be adjusted to a length that allows a urine collecting device to be connected to a subject (e.g., a subject wearing a catheter) without an excess length of tubing that might retain urine. For example, the extendable tubing may be extended or contracted in length so that there is no unnecessary slack in the tubing. The length of the extendable tubing can be extended by adjusting the outer surface of the tubing, as described above. The extendable tubing may be extended and compressed over a wide range of sizes. For example, the extendable tubing may extend from a compressed length to an extended length that is more than 1.5 times, 2 times, 2.5 times, 3 times, 5 times, or 10 times the length of the compressed length.

The inner surface of the tubing of any urine collection device (including but not limited to extendable tubing) may be made of or treated with any appropriate substance to inhibit the retention of urine within the tubing. For example, the inner surface of the tubing may be embedded, coated, or otherwise treated with a material that increases the wetability of the inner surface, and/or lowers the available surface tension of the inner surface of the tubing. In some variations, a portion of the urine collection device (e.g., the tubing) includes a surfactant to facilitate urine drainage.

Use of Urine Collection Devices

The urine collection devices and systems described herein may be used to collect urine from a subject. A urine collection device or system may include any combination or sub-combinations of the components described herein. For example, a urine collection device may include a receptacle to collect urine. The receptacle may be any appropriate receptacle having an inner volume that may be used to store urine. For example, the receptacle may be part of an expandable container having a bias. The urine collection device can further include an inlet providing access into the receptacle. The urine collection device may further include tubing for connecting to the receptacle (e.g., by connecting to the inlet). In some variations, the urine collection device may include a meter for measuring at least one characteristic of urine. In some variations, the urine collection device may further include a pump for moving urine through the tubing and into the receptacle.

In operation, any of the steps for use described herein may be performed to collect urine from a subject using the urine collection devices or systems described herein. A urine collection device may be connected to a catheter worn by a subject (e.g., by connecting the tubing of the urine collection device). Urine may then empty from the catheter, and into the tubing. If the urine collection device includes a pump, a pump may be used to move urine through the tubing. The urine may pass through a meter. The meter may measure a characteristic from the urine. For example, the meter may measure the volume, flow rate, temperature, pH, concentration of a substance, etc. The meter may hold the urine, or the urine may pass through the meter. In some variations, the meter includes a meter release for emptying the meter. The urine then passes into the receptacle, where it can be stored. In some variations, the urine may be removed from the receptacle. In some variations, the entire urine collection device is disposable.

The urine collection devices and systems described herein may also be included as part of a kit. The kit may include additional materials appropriate for using the devices. For example, a kit may include instructions for using the devices or systems. Instructions may be provided in any appropriate medium, including written, visual, pictographic, audible, or the like. In some versions, the instructions describe the methods of using the device as described above. Kits may also include additional materials (e.g., connectors, additional tubing, spare bags, etc.) useful in conjunction with the devices described herein.

While the invention has been described in terms of particular variations and illustrative figures, those of skill in the art will recognize that the invention is not limited to the variations or figures described. In addition, where methods and steps described above indicate certain events occurring in certain order, those of skill in the art will recognize that the ordering of certain steps may be modified and that such modifications are in accordance with the variations of the invention. Additionally, certain steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A fluid collection device, comprising:
    an inlet;
    a receptacle; and
    a meter fluidly connecting the inlet to the receptacle, the meter including:
        a measurement region that measures at least one characteristic from a fluid, the measurement region having a plurality of fluid-holding chambers, wherein adjacent chambers of the plurality of fluid-holding chambers are in fluid communication;
        a meter release controlling the simultaneous release of fluid from the plurality of fluid-holding chambers directly into the receptacle; and
        a plurality of ports connecting the plurality of fluid-holding chambers to the receptacle along separate fluid flow paths.

2. The fluid collection device according to claim 1, wherein the plurality of fluid-holding chambers are calibrated to measure fluid volume.

3. The fluid collection device according to claim 1, wherein the meter release is an automatic meter release.

4. The fluid collection device according to claim 1, further comprising extendible tubing having a proximal end connected to the inlet.

5. The fluid collection device according to claim 4, wherein the extendible tubing has a distal end in fluid communication with a urinary catheter insertable into a subject and the measurement region measures a characteristic of urine from a subject.

6. The fluid collection device according to claim 4, wherein the extendable tubing includes an inner wall surrounded by an outer wall, and wherein the extendable tubing has a compressed length and an extended length.

7. The fluid collection device according to claim 6, wherein the extendable tubing is adjustable to an intermediate length between the compressed length and the extended length, and can be maintained at the intermediate length.

8. The fluid collection device according to claim 6, wherein the extended length is greater than twice the length of the compressed length.

9. The fluid collection device according to claim 6, wherein the outer wall of the extendable tubing includes segments that telescope.

10. The fluid collection device according to claim 6, wherein the outer wall is configured in a shape of an accordion.

11. The fluid collection device according to claim 6, wherein the inner wall includes a smooth surface.

12. The fluid collection device according to claim 6, wherein the inner wall comprises an elastic material.

13. The fluid collection device according to claim 6, wherein the inner wall includes a surfactant.

14. The fluid collection device according to claim 1, further comprising a pump to facilitate movement of a fluid through the inlet into the meter.

15. The fluid collection device according to claim 1, wherein the receptacle comprises an expandable container, the expandable container having a contracted position and an expanded position, and a bias that converts the expandable container from the contracted position to the expanded position.

16. The fluid collection device according to claim 1, further comprising a one-way air inlet valve.

17. The fluid collection device according to claim 1, further comprising a plurality of openings, including a rotatable rod having a plurality of passages therethrough, simultaneous passage of fluid from the plurality of fluid-holding chambers of the measurement region into the receptacle through the plurality of openings enabled upon alignment of the plurality of passages with the plurality of ports and the plurality of openings by rotation of the rotatable rod about a longitudinal axis thereof.

18. A fluid collection device, comprising:
    an inlet;
    a receptacle;
    a meter fluidly connecting the inlet to the receptacle, the meter including:
        a measurement region that measures at least one characteristic from a fluid, the measurement region having a plurality of fluid-holding chambers, wherein adjacent chambers of the plurality of fluid-holding chambers are in fluid communication;
        a meter release controlling simultaneous release of fluid from the plurality of fluid-holding chambers directly into the receptacle, the meter release including a rotatable rod having a plurality of passages therethrough; and
        a plurality of ports connecting the plurality of fluid-holding chambers to the receptacle along separate fluid flow paths.

19. The fluid collection device according to claim 18, wherein the meter release opens the plurality of ports.

20. The fluid collection device according to claim 18, wherein the plurality of passages of the meter release are aligned with the plurality of ports to release fluid from the meter, and are misaligned from the plurality of ports to retain fluid within the meter.

\* \* \* \* \*